United States Patent
Wu et al.

(10) Patent No.: US 10,499,747 B2
(45) Date of Patent: Dec. 10, 2019

(54) METHOD AND DEVICE FOR CONTROLLING INTELLIGENT MATTRESS

(71) Applicant: Beijing Xiaomi Mobile Software Co., Ltd., Haidian District, Beijing (CN)

(72) Inventors: Ke Wu, Beijing (CN); Yingchun Xie, Beijing (CN); Ge Fan, Beijing (CN)

(73) Assignee: BEIJING XIAOMI MOBILE SOFTWARE CO., LTD., Beijing (CN)

( * ) Notice: Subject to any disclaimer, the term of this patent is extended or adjusted under 35 U.S.C. 154(b) by 141 days.

(21) Appl. No.: 15/698,660

(22) Filed: Sep. 8, 2017

(65) Prior Publication Data

US 2018/0070737 A1    Mar. 15, 2018

(30) Foreign Application Priority Data

Sep. 14, 2016 (CN) .......................... 2016 1 0827367

(51) Int. Cl.
*G06F 19/00* (2018.01)
*A47C 31/00* (2006.01)
*G16H 40/63* (2018.01)
*G16H 20/30* (2018.01)
*A47C 27/08* (2006.01)
(Continued)

(52) U.S. Cl.
CPC .......... *A47C 31/008* (2013.01); *A47C 27/083* (2013.01); *A61H 15/0078* (2013.01); *G06F 19/3481* (2013.01); *G16H 20/30* (2018.01); *G16H 40/63* (2018.01); *A61H 2201/0146* (2013.01); *G16H 50/20* (2018.01)

(58) Field of Classification Search
CPC ................ A47C 31/008; A47C 27/083; A61H 15/0078; A61H 2201/0146; G16H 20/30; G16H 40/63; G16H 50/20; G06F 19/3481
See application file for complete search history.

(56) References Cited

U.S. PATENT DOCUMENTS

| | | | |
|---|---|---|---|
| 2007/0016119 A1* | 1/2007 | Inada | A61H 9/0078 601/151 |
| 2013/0245389 A1 | 9/2013 | Schultz | |
| 2015/0182113 A1 | 7/2015 | Utter, II | |

(Continued)

FOREIGN PATENT DOCUMENTS

| | | |
|---|---|---|
| CN | 2451091 Y | 10/2001 |
| CN | 200984384 Y | 12/2007 |

(Continued)

OTHER PUBLICATIONS

The First Office Action in Chinese application No. 201610827367.X, dated Sep. 25, 2018.

(Continued)

*Primary Examiner* — Michael D Masinick
(74) *Attorney, Agent, or Firm* — Jun He Law Offices P.C.; James J. Zhu

(57) ABSTRACT

A method and device for controlling an intelligent mattress are provided. The method includes: acquiring motion data information of a user; analyzing the motion data information to obtain fatigue data information of the user; determining target control information according to the fatigue data information, the target control information being configured to control the intelligent mattress of the user; and sending the target control information to the intelligent mattress.

4 Claims, 9 Drawing Sheets

(51) Int. Cl.
*A61H 15/00* (2006.01)
*G16H 50/20* (2018.01)

(56) References Cited

U.S. PATENT DOCUMENTS

| | | |
|---|---|---|
| 2015/0182163 A1 | 7/2015 | Utter |
| 2015/0182164 A1 | 7/2015 | Utter, II |
| 2015/0186609 A1 | 7/2015 | Utter, II |
| 2015/0366746 A1* | 12/2015 | Ashby ............... A61H 15/0078 601/49 |
| 2016/0317074 A1 | 11/2016 | Kawai et al. |
| 2016/0317099 A1 | 11/2016 | Kawai et al. |
| 2016/0328524 A1 | 11/2016 | Kawai et al. |
| 2016/0328533 A1 | 11/2016 | Kawai et al. |
| 2016/0328534 A1 | 11/2016 | Kawai et al. |
| 2016/0335401 A1 | 11/2016 | Kawai et al. |
| 2016/0335402 A1 | 11/2016 | Kawai et al. |
| 2017/0135495 A1 | 5/2017 | Hattori |
| 2017/0135881 A1* | 5/2017 | Franceschetti ......... A61G 7/018 |
| 2017/0136348 A1 | 5/2017 | Hattori et al. |
| 2017/0308046 A1 | 10/2017 | Li et al. |

FOREIGN PATENT DOCUMENTS

| | | |
|---|---|---|
| CN | 202775285 U | 3/2013 |
| CN | 104665406 A | 6/2015 |
| CN | 105853136 A | 8/2016 |
| DE | 202009004803 U1 | 8/2010 |
| DE | 202009004655 U1 | 9/2018 |
| EP | 2881013 A1 | 6/2015 |
| EP | 3096235 A1 | 11/2016 |
| EP | 3235484 A1 | 10/2017 |
| WO | 2015107748 A1 | 7/2015 |

OTHER PUBLICATIONS

Supplementary European Search Report in European application No. 17189643.4, dated Feb. 1, 2018.

* cited by examiner

METHOD AND DEVICE FOR CONTROLLING INTELLIGENT MATTRESS

CROSS-REFERENCE TO RELATED APPLICATIONS

This application is filed based upon and claims priority to Chinese Patent Application No. 201610827367.X, filed on Sep. 14, 2016, the entire contents of which are incorporated herein by reference.

TECHNICAL FIELD

The present disclosure generally relates to intelligent mattresses, and more particularly, to a method and a device for controlling an intelligent mattress.

BACKGROUND

An intelligent mattress integrates multiple functions, including angle adjustment, temperature adjustment, hardness selection, far infrared and massaging functions, a lifting function including free adjustment of seven major parts of the head, the neck, the shoulders, the back, the waist, the hips and the legs, the massaging function including a rolling type massaging system, far infrared heating including balanced, stable and variable frequency far infrared heating, gyromagnetic physiotherapy and the like.

However, a typical intelligent mattress is required to be manually regulated, and is not intelligent enough. When going back home after an exhausted day, a user has to regulate an expected massaging or mattress angle according to his/her own feeling. In addition, the found angle may also be unscientific, and is very likely to get overcorrect to cause unnecessary injuries to the body or bones and muscles, so that an expected effect cannot be achievable.

SUMMARY

According to a first aspect of the embodiments of the present disclosure, there is provided a method for controlling an intelligent mattress, comprising: acquiring motion data information of a user; analyzing the motion data information to obtain fatigue data information of the user; determining target control information according to the fatigue data information, the target control information being configured to control the intelligent mattress of the user; and sending the target control information to the intelligent mattress.

According to a second aspect of the embodiments of the present disclosure, there is provided a method for controlling an intelligent mattress, which is applied to the intelligent mattress and includes: receiving target control information sent by a server; and running according to the target control information.

According to a third aspect of the embodiments of the present disclosure, there is provided a device for controlling an intelligent mattress, which is applied to a server and includes: a processor; and a memory configured to store instructions executable by the processor, wherein the processor is configured to: acquire motion data information of a user; analyze the motion data information to obtain fatigue data information of the user; determine target control information according to the fatigue data information, the target control information being configured for the user to control the intelligent mattress; and send the target control information to the intelligent mattress.

It should be understood that the above general descriptions and detailed descriptions below are only exemplary and explanatory and not intended to limit the present disclosure.

BRIEF DESCRIPTION OF THE DRAWINGS

The accompanying drawings, which are incorporated in and constitute a part of this specification, illustrate embodiments consistent with the present disclosure and, together with the description, serve to explain the principles of the present disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the present disclosure. Instead, they are merely examples of apparatuses and methods consistent with aspects related to the present disclosure as recited in the appended claims.

An embodiment of the present disclosure provides a method for controlling an intelligent mattress, and the method may be applied to a server.

Figure 1:
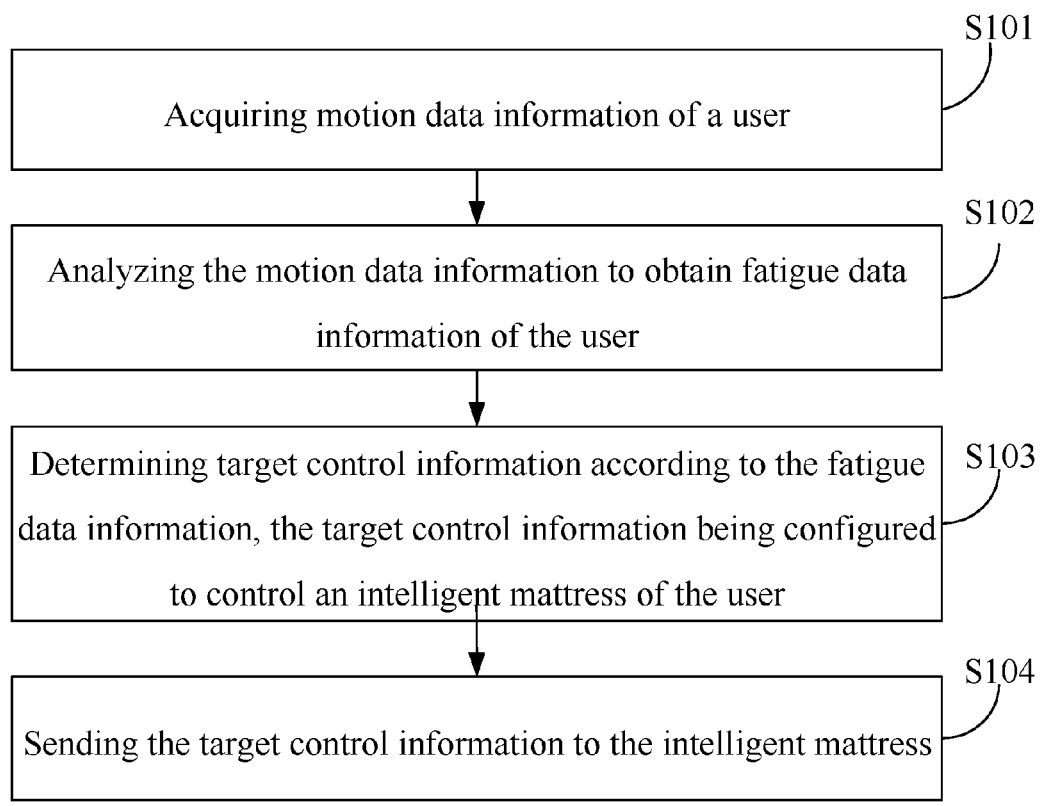
FIG. 1 is a flow chart showing a method for controlling an intelligent mattress according to an exemplary embodiment.

FIG. 1 is a flow chart showing a method for controlling an intelligent mattress according to an exemplary embodiment.

As shown in FIG. 1, the method includes Steps S101-S104.

In Step S101, motion data information of a user is acquired.

In an embodiment, the motion data information includes motion part information and corresponding motion intensity information.

Herein, the motion part information refers to a motion part of the user. Specifically, the motion part information may be directly acquired. Motion type information of the user may also be acquired, such as a motion type of swimming, running, ball playing, sit-up and the like, and the motion part information of the user is further determined according to the motion type information. For example, arms and legs are determined as motion parts through swimming, running, ball playing and the like, whereas the abdomen, the upper body and the like are determined as motion parts through sit-up.

In Step S102, the motion data information is analyzed to obtain fatigue data information of the user.

Herein, the fatigue data information includes fatigue part information and corresponding fatigue degree information.

The fatigue data information of the user may be determined by analyzing the motion data information of the user. For example, the fatigue part information may be determined through the motion part information of the user. That is, the motion part of the user may be a fatigue part. The fatigue degree information of the user may be determined through the motion intensity information of the user. The motion intensity information is positively related to the fatigue degree information. That is, if fatigue intensity is higher, a fatigue degree is correspondingly higher.

In Step S103, target control information is determined according to the fatigue data information, the target control information being configured to control the intelligent mattress of the user.

Herein, the target control information is configured to control a massage region, massage time length and working mode of the intelligent mattress.

The target control information may be determined according to the fatigue data information of the user. For example, a region corresponding to the fatigue part on the intelligent mattress may be determined as the massage region according to the fatigue part of the user, and the massage time length, the working mode and the like may be determined according to a fatigue degree of the user. For example, if the arms and the legs are fatigue parts of the user, regions corresponding to the arms and the legs on the intelligent mattress are regions required to be massaged. If the user feels especially fatigue, the corresponding massage time length may be determined to be relatively larger, and the working mode may be a strong working mode. If the user feels a little fatigue, the corresponding massage time length may be determined to be relatively smaller, and the working mode may be a gentle working mode. Therefore, different massage requirements of different users are met.

In Step S104, the target control information is sent to the intelligent mattress.

The server sends the determined target control information to the intelligent mattress, and then the intelligent mattress may run according to the target control information.

In the embodiment, the server acquires the motion data information of the user, determines the fatigue data information of the user according to the motion data information of the user, further determines the target control information according to the fatigue data information, and controls the intelligent mattress of the user through the target control information. In such a manner, the target control information for the intelligent mattress may be directly determined according to the motion data information of the user, and the user is not required to perform manual setting, regulation and the like. Operations of the user are reduced. Meanwhile, different massage requirements of different users may also be met. Most healthy and proper intelligent mattress control information is selected for the user, and user experiences are improved.

Figure 2:
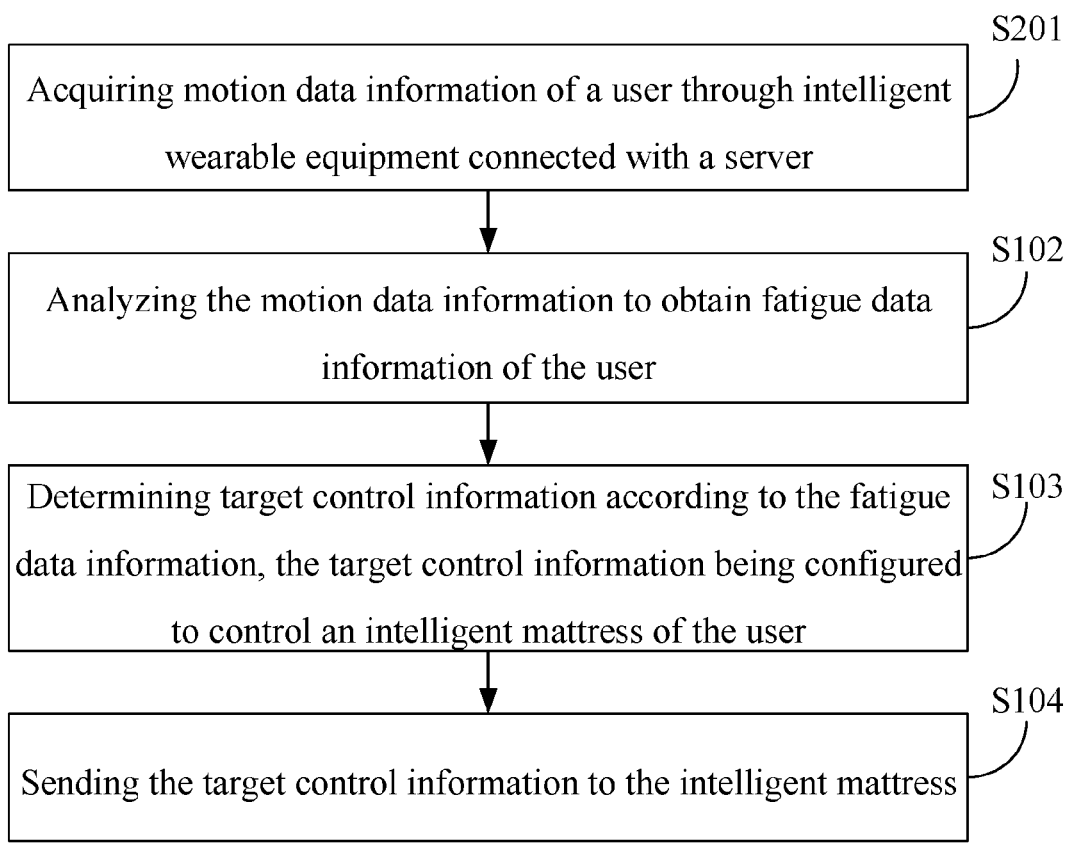
FIG. 2 is a flow chart showing another method for controlling an intelligent mattress according to an exemplary embodiment.

FIG. 2 is a flow chart showing another method for controlling an intelligent mattress according to an exemplary embodiment.

As shown in FIG. 2, in an embodiment, Step S101 includes Step S201.

In Step S201, the motion data information of the user is acquired through intelligent wearable equipment connected with the server.

In the embodiment, the motion data information of the user may be acquired through the intelligent wearable equipment connected with the server. That is, the motion part information and motion intensity information of the user are acquired. Herein, the motion part information and motion intensity information of the user may be directly acquired through the intelligent wearable equipment. For example, the intelligent wearable equipment acquires changes of each part of the body during motion of the user, determines the motion part of the user, determines the motion intensity according to a change degree, or determines the motion intensity according to a recorded motion time length and the like of the user.

Of course, the intelligent wearable equipment may also acquire the motion type information of the user, such as the motion type of swimming, running, ball playing, sit-up and the like, and further determines the motion part information of the user according to the motion type information. For example, arms and legs are determined as motion parts through swimming, running, ball playing and the like, and the abdomen, the upper body and the like are determined as motion parts through sit-up.

Herein, the user may perform association, binding or the like on the server, its own intelligent wearable equipment and the intelligent mattress before use.

Figure 3:
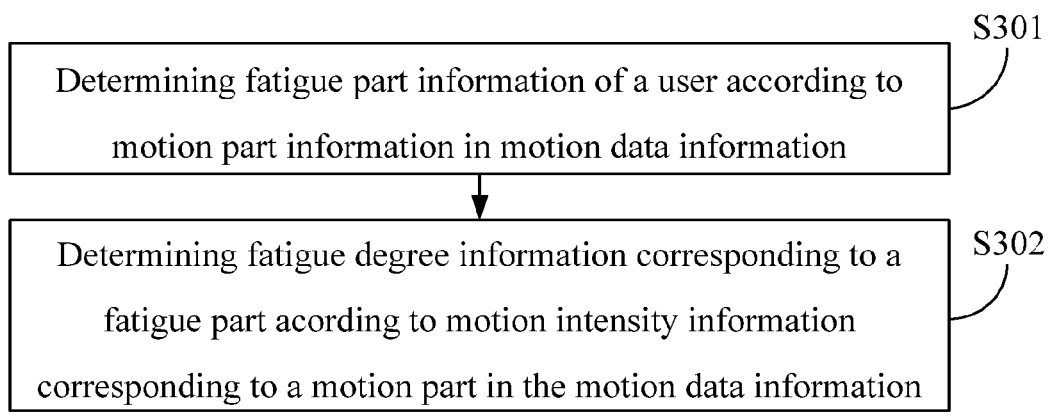
FIG. 3 is a flow chart showing Step S102 in a method for controlling an intelligent mattress according to an exemplary embodiment.

FIG. 3 is a flow chart showing Step S102 in a method for controlling an intelligent mattress according to an exemplary embodiment.

As shown in FIG. 3, in an embodiment, Step S102 includes Steps S301-S302.

In Step S301, the fatigue part information of the user is determined according to the motion part information in the motion data information.

The fatigue part information may be determined through the motion part information of the user. That is, the motion part of the user is the fatigue part.

In Step S302, determining the fatigue degree information corresponding to a fatigue part according to the motion intensity information corresponding to a motion part in the motion data information.

Herein, the user or a manufacturer may preset fatigue degree information corresponding to different motion intensity information. For example, motion intensities are divided into a first level, a second level, a third level, a fourth level and the like. When the motion intensity is at the first level, the corresponding fatigue degree is also at the first level. When the motion intensity is at the second level, the corresponding fatigue degree is also at the second level. When the motion intensity is at the third level, the corresponding fatigue degree is also at the third level. When the motion intensity is at the fourth level, the corresponding fatigue degree is also at the fourth level, etc. In such a manner, the fatigue degree information corresponding to the motion intensity information is determined according to a relationship between motion intensity information and fatigue degree information.

Figure 4:
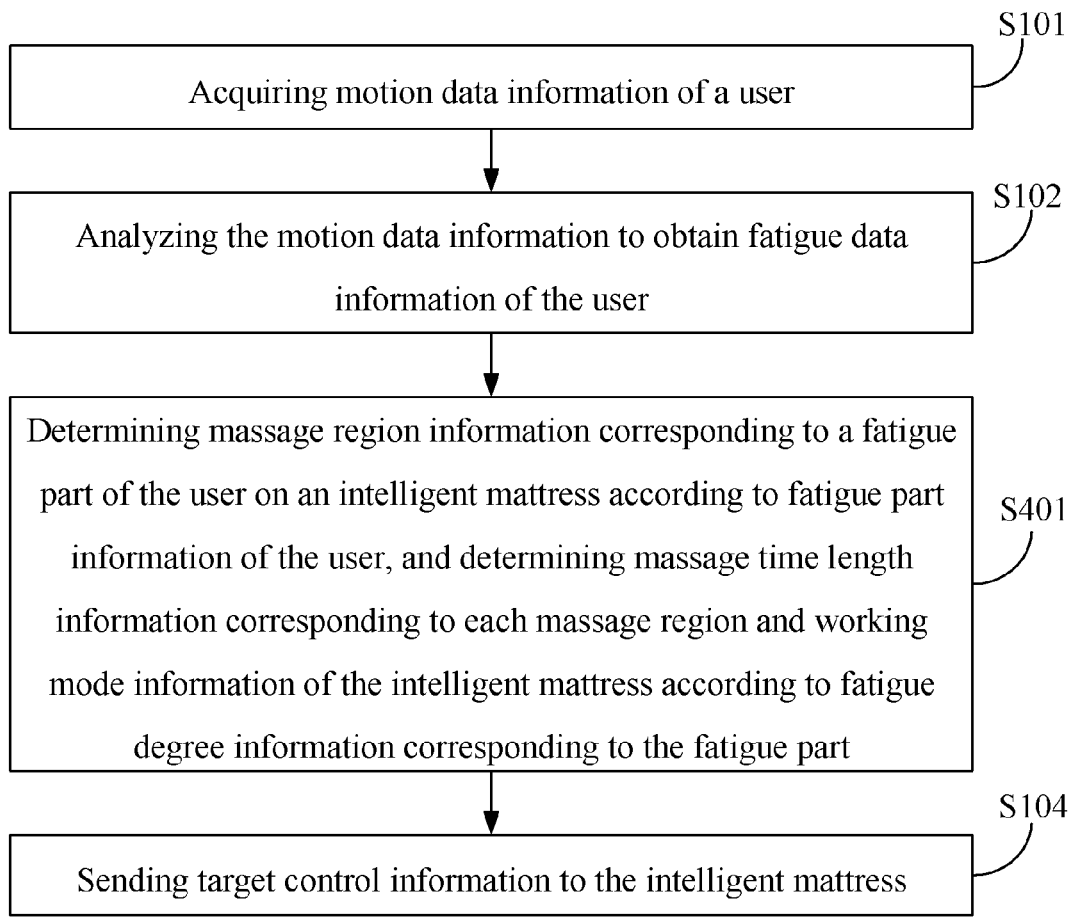
FIG. 4 is a flow chart showing another method for controlling an intelligent mattress according to an exemplary embodiment.

FIG. 4 is a flow chart showing another method for controlling an intelligent mattress according to an exemplary embodiment.

As shown in FIG. 4, in an embodiment, Step S103 includes Step S401.

In Step S401, massage region information corresponding to the fatigue part of the user on the intelligent mattress is determined according to the fatigue part information of the user, and massage time length information corresponding to each massage region and working mode information of the intelligent mattress are determined according to the fatigue degree information corresponding to the fatigue part.

Herein, the working mode of the intelligent mattress may be the strong working mode, an ordinary working mode, the gentle working mode and the like. Massage force in the strong working mode is relatively stronger, and massage force in the gentle working mode is relatively weaker.

The region corresponding to the fatigue part on the intelligent mattress may be determined as the massage region according to the fatigue part of the user, and the massage time length, the working mode and the like may be determined according to the fatigue degree of the user. For example, if the arms and the legs are fatigue parts of the user, regions corresponding to the arms and the legs on the intelligent mattress are regions required to be massaged. If the user feels especially fatigue, the corresponding massage time length may be determined to be relatively larger, and the working mode may be the strong working mode. If the user feels a little fatigue, the corresponding massage time length may be determined to be relatively smaller, and the working mode may be the gentle working mode. Therefore, different massage requirements of different users are met.

Herein, the user or the manufacturer may preset massage time lengths and working modes corresponding to different fatigue degrees. For example, when the fatigue degree is at the first level, the corresponding massage time length is 10 minutes, and the corresponding working mode is the gentle working mode. When the fatigue degree is at the second level, the corresponding massage time length is 20 minutes, and the corresponding working mode is the ordinary working mode. When the fatigue degree is at the third level, the corresponding massage time length is 30 minutes, and the corresponding working mode is the ordinary working mode. When the fatigue degree is at the fourth level, the corresponding massage time length is 30 minutes, and the corresponding working mode is the strong working mode. Of course, it may also be set that the working mode continuously changes along with a change of the massage time length. For example, when the fatigue degree is at the fourth level, the corresponding massage time length is 30 minutes, wherein the strong working mode is adopted in the first 10 minutes, the ordinary working mode is adopted in the next 10 minutes, and the gentle working mode is adopted in the last 10 minutes, so that a better massage experience may be provided for the user. In such a manner, the massage time length information and working mode information corresponding to the fatigue degree information may be determined according to a relationship among fatigue degree information, massage time length information and working mode information.

An embodiment of the present disclosure further provides a method for controlling an intelligent mattress. The method may be applied to the intelligent mattress.

Figure 5:
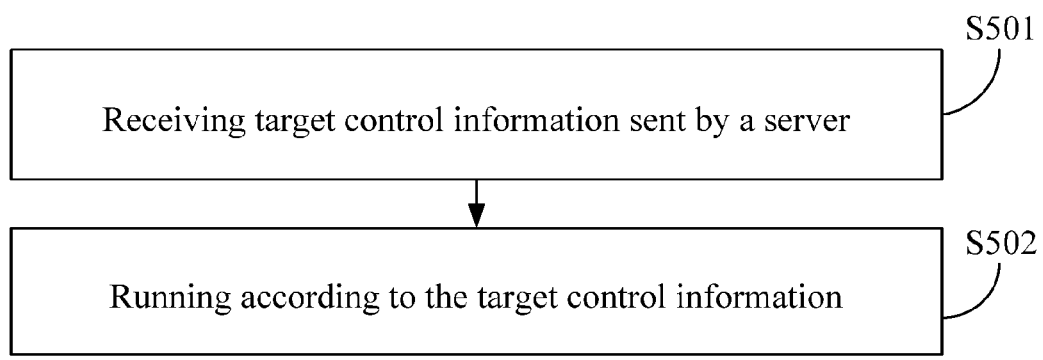
FIG. 5 is a flow chart showing another method for controlling an intelligent mattress according to an exemplary embodiment.

FIG. 5 is a flow chart showing a method for controlling an intelligent mattress according to an exemplary embodiment.

As shown in FIG. 5, the method includes Step S501-S502.

In Step S501, target control information sent by a server is received.

In Step S502, it is running according to the target control information.

In the embodiment, the server acquires motion data information of a user, determines fatigue data information of the user according to the motion data information of the user, further determines the target control information according to the fatigue data information, and controls the intelligent mattress of the user through the target control information. In such a manner, the target control information for the intelligent mattress may be directly determined according to the motion data information of the user, and the user is not required to perform manual setting, regulation and the like, so that operations of the user are reduced. Meanwhile, different massage requirements of different users may also be met. Most healthy and proper intelligent mattress control information is selected for the user, and user experiences are improved.

In an embodiment, the target control information is configured to control each massage region, massage time length and working mode of the intelligent mattress.

In the embodiment, the target control information may be massage region information, massage time length information, working mode information and the like of the intelligent mattress. Herein, the working mode information may be a massage mode, such as a gentle working mode and a strong working mode, and of course, may also be a sleep mode, a power-saving mode and the like. The target control information may, of course, also be other control information such as information of an angle and amplitude of each part of the mattress, besides the abovementioned information.

The below is a device embodiment of the present disclosure, which may be configured to execute the method embodiment of the present disclosure.

Figure 6:
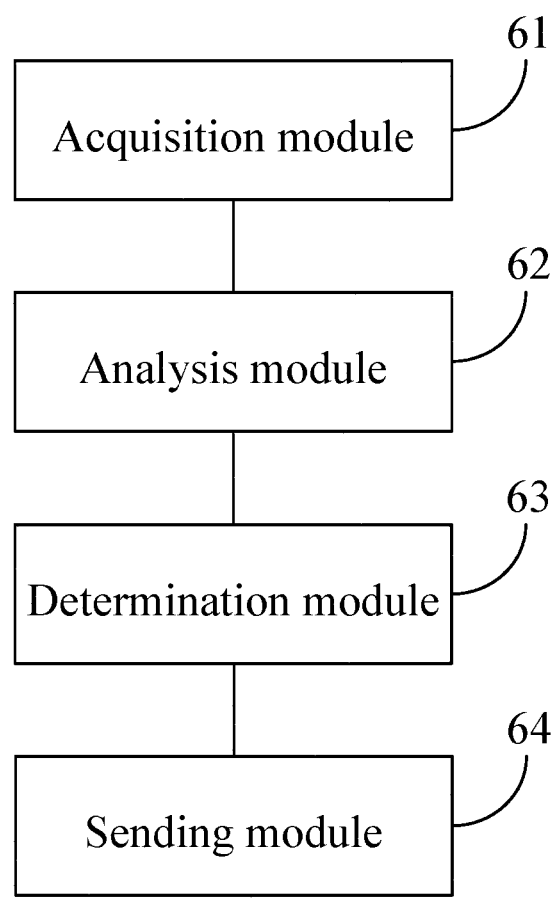
FIG. 6 is a block diagram illustrating a device for controlling an intelligent mattress according to an exemplary embodiment.

FIG. 6 is a block diagram illustrating a device for controlling an intelligent mattress according to an exemplary embodiment. The device may be implemented into part or all of a server through software, hardware or a combination thereof. As shown in FIG. 6, the device for controlling the intelligent mattress includes an acquisition module 61, an analysis module 62, a determination module 63 and a sending module 64.

The acquisition module 61 is configured to acquire motion data information of a user.

In an embodiment, the motion data information includes motion part information and corresponding motion intensity information.

Herein, the motion part information refers to a motion part of the user. Specifically, the motion part information may be directly acquired. Motion type information of the user may also be acquired, such as a motion type of swimming, running, ball playing, sit-up and the like, and the motion part information of the user is further determined according to the motion type information. For example, arms and legs are determined as motion parts through swimming, running, ball playing and the like, and the abdomen, the upper body and the like are determined as motion parts through sit-up.

The analysis module 62 is configured to analyze the motion data information to obtain fatigue data information of the user.

Herein, the fatigue data information includes fatigue part information and corresponding fatigue degree information.

The fatigue data information of the user may be determined by analyzing the motion data information of the user. For example, the fatigue part information may be determined through the motion part information of the user. That is, the motion part of the user may be a fatigue part. The fatigue degree information of the user may be determined through the motion intensity information of the user. The motion intensity information is positively related to the fatigue degree information. That is, if a fatigue intensity is higher, a fatigue degree is correspondingly higher.

The determination module 63 is configured to determine target control information according to the fatigue data information, the target control information being configured to control the intelligent mattress of the user.

Herein, the target control information is configured to control each massage region, massage time length and working mode of the intelligent mattress.

The target control information may be determined according to the fatigue data information of the user. For example, a region corresponding to the fatigue part on the intelligent mattress may be determined as the massage region according to the fatigue part of the user. The massage time length, the working mode and the like may be determined according to a fatigue degree of the user. For example, if the arms and the legs are fatigue parts of the user, regions corresponding to the arms and the legs on the intelligent mattress are regions required to be massaged. If the user feels especially fatigue, the corresponding massage time length may be determined to be relatively larger, and the working mode may be a strong working mode. If the user feels a little fatigue, the corresponding massage time length may be determined to be relatively smaller, and the working mode may be a gentle working mode. Therefore, different massage requirements of different users are met.

A sending module 64 is configured to send the target control information to the intelligent mattress.

The server sends the determined target control information to the intelligent mattress, and then the intelligent mattress may run according to the target control information.

In the embodiment, the server acquires the motion data information of the user, determines the fatigue data information of the user according to the motion data information of the user, further determines the target control information according to the fatigue data information, and controls the intelligent mattress of the user through the target control information. As such, the target control information for the intelligent mattress may be directly determined according to the motion data information of the user, and the user is not required to perform manual setting, regulation and the like, so that operations of the user are reduced. Meanwhile, different massage requirements of different users may also be met. Most healthy and proper intelligent mattress control information is selected for the user, and user experiences are improved.

In an embodiment, the acquisition module 61 is configured to acquire the motion data information of the user through intelligent wearable equipment connected with the server.

In the embodiment, the motion data information of the user may be acquired through the intelligent wearable equipment connected with the server. That is, the motion part information and motion intensity information of the user are acquired. Wherein, the motion part information and motion intensity information of the user may be directly acquired through the intelligent wearable equipment. For example, the intelligent wearable equipment acquires changes of each part of the body during motion of the user, determines the motion part of the user, determines the motion intensity according to a change degree, or determines the motion intensity according to a recorded motion time length and the like of the user.

Of course, the intelligent wearable equipment may also acquire the motion type information of the user, such as the motion type of swimming, running, ball playing, sit-up and the like, and further determines the motion part information of the user according to the motion type information. For example, arms and legs are determined as motion parts through swimming, running, ball playing and the like, and the abdomen, the upper body and the like are determined as motion parts through sit-up.

Herein, the user may perform association, binding or the like on the server, his own intelligent wearable equipment and the intelligent mattress before use.

Figure 7:
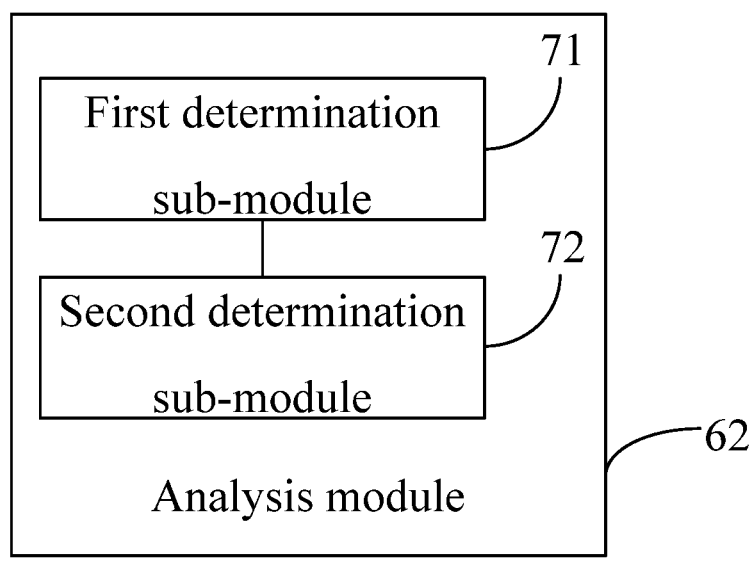
FIG. 7 is a block diagram illustrating an analysis module in a device for controlling an intelligent mattress according to an exemplary embodiment.

FIG. 7 is a block diagram illustrating an analysis module in a device for controlling an intelligent mattress according to an exemplary embodiment.

As shown in FIG. 7, in an embodiment, the analysis module 62 includes:

a first determination sub-module 71, configured to determine the fatigue part information of the user according to the motion part information in the motion data information.

The fatigue part information may be determined through the motion part information of the user. That is, the motion part of the user is the fatigue part.

A second determination sub-module 72 is configured to determine the fatigue degree information corresponding to a fatigue part according to the motion intensity information corresponding to a motion part in the motion data information.

Herein, the user or a manufacturer may preset fatigue degree information corresponding to different motion intensity information. For example, motion intensities are divided into a first level, a second level, a third level, a fourth level and the like. When the motion intensity is at the first level, the corresponding fatigue degree is also at the first level. When the motion intensity is at the second level, the corresponding fatigue degree is also at the second level. When the motion intensity is at the third level, the corresponding fatigue degree is also at the third level. When the motion intensity is at the fourth level, the corresponding fatigue degree is also at the fourth level, etc. In such a manner, the fatigue degree information corresponding to the motion intensity information is determined according to a relationship between motion intensity information and fatigue degree information.

In an embodiment, the determination module 63 is configured to determine massage region information corresponding to the fatigue part of the user on the intelligent mattress according to the fatigue part information of the user, and determine massage time length information corresponding to each massage region and working mode information of the intelligent mattress according to the fatigue degree information corresponding to the fatigue part.

Herein, the working mode of the intelligent mattress may be the strong working mode, an ordinary working mode, the gentle working mode and the like. Massage force in the strong working mode is relatively stronger, and massage force in the gentle working mode is relatively weaker.

The region corresponding to the fatigue part on the intelligent mattress may be determined as the massage region according to the fatigue part of the user, and the massage time length, the working mode and the like may be determined according to the fatigue degree of the user. For example, if the arms and the legs are fatigue parts of the user, regions corresponding to the arms and the legs on the intelligent mattress are regions required to be massaged. If the user feels especially fatigue, the corresponding massage time length may be determined to be relatively larger, and the working mode may be the strong working mode. If the user feels a little fatigue, the corresponding massage time length may be determined to be relatively smaller, and the working mode may be the gentle working mode. Therefore, different massage requirements of different users are met.

Herein, the user or the manufacturer may preset massage time lengths and working modes corresponding to different fatigue degrees. For example, when the fatigue degree is at the first level, the corresponding massage time length is 10 minutes, and the corresponding working mode is the gentle working mode. When the fatigue degree is at the second level, the corresponding massage time length is 20 minutes, and the corresponding working mode is the ordinary working mode. When the fatigue degree is at the third level, the corresponding massage time length is 30 minutes, and the corresponding working mode is the ordinary working mode. When the fatigue degree is at the fourth level, the corresponding massage time length is 30 minutes, and the corresponding working mode is the strong working mode. Of course, it may also be set that the working mode continuously changes along with a change of the massage time length. For example, when the fatigue degree is at the fourth level, the corresponding massage time length is 30 minutes, wherein the strong working mode is adopted in the first 10 minutes, the ordinary working mode is adopted in the next 10 minutes, and the gentle working mode is adopted in the last 10 minutes, so that a better massage experience may be provided for the user. In such a manner, the massage time length information and working mode information corresponding to the fatigue degree information may be determined according to a relationship among fatigue degree information, massage time length information and working mode information.

Figure 8:
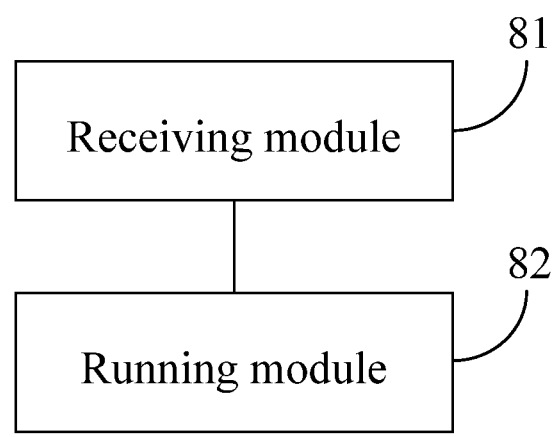
FIG. 8 is a block diagram illustrating a device for controlling an intelligent mattress according to an exemplary embodiment.

FIG. 8 is a block diagram illustrating a device for controlling an intelligent mattress according to an exemplary embodiment. The device may be implemented into part or the entire of the intelligent mattress through software, hardware or a combination thereof. As shown in FIG. 8, the device for controlling the intelligent mattress includes: a receiving module 81 configured to receive target control information sent by a server; and a running module 82 configured to run according to the target control information.

In the embodiment, the server acquires motion data information of a user, determines fatigue data information of the user according to the motion data information of the user, further determines the target control information according to the fatigue data information, and controls the intelligent mattress of the user through the target control information. In such a manner, the target control information for the intelligent mattress may be directly determined according to the motion data information of the user, and the user is not required to perform manual setting, regulation and the like, so that operations of the user are reduced. Meanwhile, different massage requirements of different users may also be met. Most healthy and proper intelligent mattress control information is selected for the user, and user experiences are improved.

In an embodiment, the target control information is configured to control each massage region, massage time length and working mode of the intelligent mattress.

In the embodiment, the target control information may be massage region information, massage time length information, working mode information and the like of the intelligent mattress. Herein, the working mode information may be a massage working mode, such as a gentle working mode and a strong working mode, and of course, may also be a sleep mode, a power-saving mode and the like. The target control information may, of course, also be other control information such as information of an angle and amplitude of each part of the mattress, besides the abovementioned information.

According to a fifth aspect of the embodiments of the present disclosure, a device for controlling an intelligent mattress is provided, which is applied to a server and includes: a processor; and a memory configured to store instructions executable by the processor. The processor is configured to: acquire motion data information of a user; analyze the motion data information to obtain fatigue data information of the user; determine target control information according to the fatigue data information, the target control information being configured for the user to control the intelligent mattress; and send the target control information to the intelligent mattress.

The processor may further be configured to: acquire the motion data information of the user through intelligent wearable equipment connected with a server.

The motion data information includes motion part information and corresponding motion intensity information. The fatigue data information includes fatigue part information and corresponding fatigue degree information. The target control information is configured to control each massage region, massage time length and working mode of the intelligent mattress.

The processor may further be configured to: determine the fatigue part information of the user according to the motion part information in the motion data information; and determine the fatigue degree information corresponding to a fatigue part according to the motion intensity information corresponding to a motion part in the motion data information.

The processor may further be configured to determine massage region information corresponding to the fatigue part of the user on the intelligent mattress according to the fatigue part information of the user, and determine massage time length information corresponding to each massage region and working mode information of the intelligent mattress according to the fatigue degree information corresponding to the fatigue part.

According to a sixth aspect of the embodiments of the present disclosure, a device for controlling an intelligent mattress is provided, which is applied to the intelligent mattress and includes: a processor; and a memory configured to store instructions executable by the processor. The processor is configured to: receive target control information sent by a server; and run according to the target control information. The target control information is configured to control each massage region, massage time length and working mode of the intelligent mattress.

Figure 9:
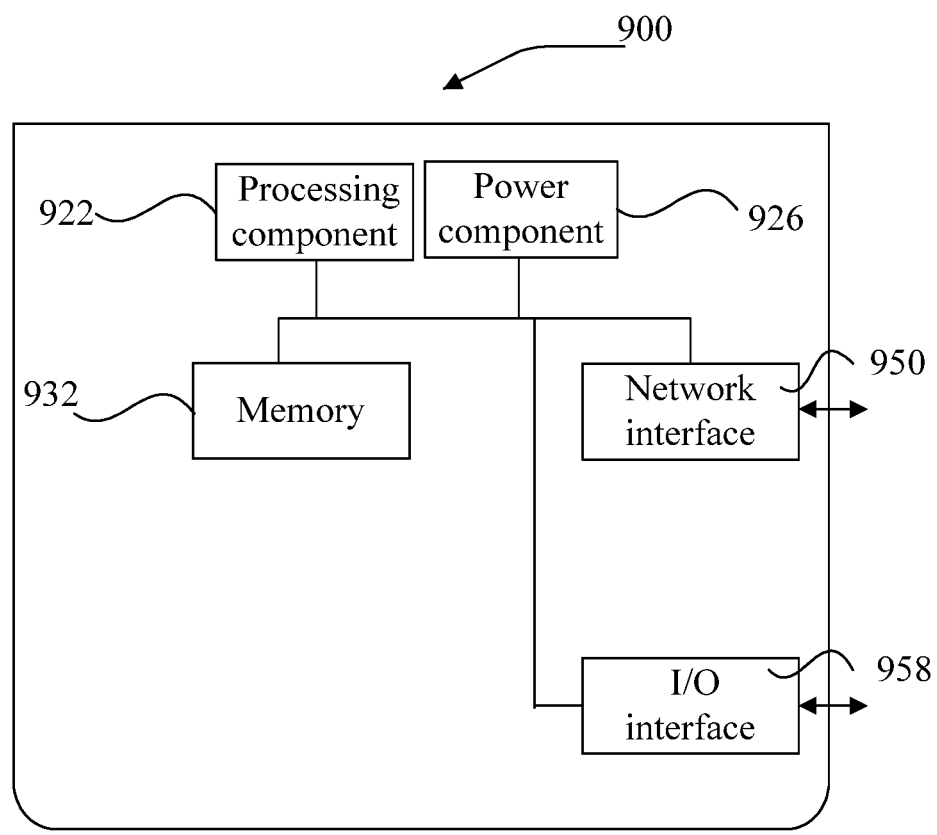
FIG. 9 is a block diagram illustrating a device for controlling an intelligent mattress according to an exemplary embodiment.

FIG. 9 is a block diagram illustrating a device for controlling an intelligent mattress according to an exemplary embodiment. For example, the device 900 may be provided as a server. The device 900 includes a processing component 922, further including one or more processors, and a memory resource represented by a memory 932, configured to store instructions executable by the processing component 922, such as application programs. The application programs stored in the memory 932 may include one or more than one module of which each corresponds to a set of instructions. In addition, the processing component 922 is configured to execute the instructions so as to execute the abovementioned method.

The device 900 may further include a power component 926 configured to execute power management of the device 900, a wired or wireless network interface 950 configured to connect the device 900 to a network, and an Input/Output (I/O) interface 958. The device 900 may be operated on the basis of an operating system stored in the memory 932, such as Windows Server™, Mac OS X™, Unix™, Linux™ or FreeBSD™.

A non-transitory computer-readable storage medium is provided, and instructions in the storage medium are executed by the processor of the device 900 to enable the device 900 to execute the abovementioned method for controlling the intelligent mattress, the method including: acquiring motion data information of a user; analyzing the motion data information to obtain fatigue data information of the user; determining target control information according to the fatigue data information, the target control information being configured to control the intelligent mattress of the user; and sending the target control information to the intelligent mattress.

In an embodiment, acquiring the motion data information of the user includes: acquiring the motion data information of the user through intelligent wearable equipment connected with a server.

In an embodiment, the motion data information includes motion part information and corresponding motion intensity information, the fatigue data information includes fatigue part information and corresponding fatigue degree information, and the target control information is configured to control each massage region, massage time length and working mode of the intelligent mattress.

In an embodiment, analyzing the motion data information to obtain the fatigue data information of the user includes: determining the fatigue part information of the user according to the motion part information in the motion data information; and determining the fatigue degree information corresponding to a fatigue part according to the motion intensity information corresponding to a motion part in the motion data information.

In an embodiment, determining the target control information of the intelligent mattress according to the fatigue data information includes: determining massage region information corresponding to the fatigue part of the user on the intelligent mattress according to the fatigue part information of the user, and determining massage time length information corresponding to each massage region and working mode information of the intelligent mattress according to the fatigue degree information corresponding to the fatigue part.

Other embodiments of the present disclosure will be apparent to those skilled in the art from consideration of the specification and practice of the present disclosure disclosed herein. This application is intended to cover any variations, uses, or adaptations of the present disclosure following the general principles thereof and including such departures from the present disclosure as come within known or customary practice in the art. It is intended that the specification and examples be considered as exemplary only, with a true scope and spirit of the present disclosure being indicated by the following claims.

It will be appreciated that the present disclosure is not limited to the exact construction that has been described above and illustrated in the accompanying drawings, and that various modifications and changes can be made without departing from the scope thereof. It is intended that the scope of the present disclosure only be limited by the appended claims.

What is claimed is:

1. A method for controlling an intelligent mattress, applied to a server and comprising:
   acquiring motion data information of a user, wherein the motion data information comprises motion part information and corresponding motion intensity information;
   analyzing the motion data information to obtain fatigue data information of the user, wherein the fatigue data information comprises fatigue part information and corresponding fatigue degree information, and analyzing the motion data information to obtain the fatigue data information of the user comprises:
      determining the fatigue part information of the user according to the motion part information in the motion data information; and
      determining the fatigue degree information corresponding to the fatigue part according to the motion intensity information corresponding to the motion part in the motion data information;
   determining target control information according to the fatigue data information, wherein the target control information comprises massage region information, massage time length information and working mode information, and is configured to control each massage region, massage time length and working mode of the intelligent mattress of the user, and determining the target control information of the intelligent mattress according to the fatigue data information comprises:
      determining massage region information corresponding to the fatigue part of the user on the intelligent mattress according to the fatigue part information of the user; and
      determining massage time length information corresponding to each massage region and working mode information of the intelligent mattress according to the fatigue degree information corresponding to the fatigue part; and
   sending the target control information to the intelligent mattress.

2. The method of claim 1, wherein acquiring the motion data information of the user comprises:
   acquiring the motion data information of the user through intelligent wearable equipment connected with the server.

3. A device for controlling an intelligent mattress, applied to a server and comprising:
   a processor; and
   a memory configured to store instructions executable by the processor,
   wherein the processor is configured to:
      acquire motion data information of a user, wherein the motion data information comprises motion part information and corresponding motion intensity information;
      analyze the motion data information to obtain fatigue data information of the user, wherein the fatigue data information comprises fatigue part information and corresponding fatigue degree information, and the processor is further configured to:
         determine the fatigue part information of the user according to the motion part information in the motion data information; and
         determine the fatigue degree information corresponding to the fatigue part according to the motion intensity information corresponding to the motion part in the motion data information;
      determine target control information according to the fatigue data information, wherein the target control information comprises massage region information, massage time length information and working mode information, and is configured to control each massage region, massage time length and working mode of the intelligent mattress, and the processor is further configured to:
- determine massage region information corresponding to the fatigue part of the user on the intelligent mattress according to the fatigue part information of the user; and
- determine massage time length information corresponding to each massage region and working mode information of the intelligent mattress according to the fatigue degree information corresponding to the fatigue part; and
- send the target control information to the intelligent mattress.

4. The device of claim 3, wherein the processor configured to acquire the motion data information of the user is further configured to:
- acquire the motion data information of the user through intelligent wearable equipment connected with the server.

* * * * *